United States Patent [19]

Dürner

[11] 4,155,250
[45] May 22, 1979

[54] VISCOMETER

[76] Inventor: Herbert Dürner, Am Gasteig 14, D-8121 Pähl, Fed. Rep. of Germany

[21] Appl. No.: 911,782

[22] Filed: Jun. 2, 1978

[30] Foreign Application Priority Data

Dec. 5, 1977 [DE] Germany .................. 2754075

[51] Int. Cl.² ........................ G01N 11/10; G01N 3/24
[52] U.S. Cl. ........................................... 73/60; 73/841
[58] Field of Search .................... 73/60, 57, 841, 54

[56] References Cited

U.S. PATENT DOCUMENTS

| 2,625,034 | 1/1953 | Patterson, Jr. | 73/57 |
| 3,406,567 | 10/1968 | Terry | 73/841 |

FOREIGN PATENT DOCUMENTS

| 895538 | 9/1953 | Fed. Rep. of Germany | 73/57 |
| 931199 | 7/1955 | Fed. Rep. of Germany | 73/60 |
| 361425 | 12/1972 | U.S.S.R. | 73/54 |

Primary Examiner—Richard C. Queisser
Assistant Examiner—Joseph W. Roskos
Attorney, Agent, or Firm—Peter K. Kontler

[57] ABSTRACT

A viscometer wherein a sample of the material to be tested is introduced into the annular clearance between a stationary cylinder and a vertical shaft which carries several weights. As the shaft descends at a speed which is a function of the combined mass of weights and the viscosity of the sample in the clearance, successive weights are automatically detached from the shaft, either by piling up on top of each other after the lowermost weight comes to rest on a platform, or by being intercepted by plates which are mounted at different levels. Means is provided for centering the weights prior to start of a multi-stage test and for returning the shaft and the weights to starting positions upon completion of a multi-stage test.

23 Claims, 6 Drawing Figures

VISCOMETER

BACKGROUND OF THE INVENTION

The present invention relates to apparatus for ascertaining the rheologic properties of flowable materials. More particularly, the invention relates to improvements in viscometers of the type wherein the material to be tested is subjected to shearing stresses and the test involves determination of the speed at which the material is deformed in response to such stresses. Still more particularly, the invention relates to improvements in viscometers of the type wherein a weighted measuring element (e.g., a cord, strip, band, rod or shaft) moves relative to a stationary measuring element and a sample of the material to be tested is introduced between the stationary and mobile measuring elements.

In viscometers of the just outlined character, the mobile measuring element (i.e., the aforementioned rod, shaft, cord, band or strip) moves with some clearance through a circular or slit-shaped hole of the stationary measuring element and a sample of the material to be tested is introduced into such clearance. As the mobile element moves relative to the stationary element, the sample is subjected to shearing stresses and the velocity of the mobile element is an indicator of the viscosity of the sample.

In order to allow for convenient and more accurate plotting of a curve which denotes the viscosity of tested material, it is necessary to carry out several tests, preferably at least four successive tests during each of which the sample is subjected to a different shearing stress. When the mobile measuring element is moved by resorting to weights, it is necessary to connect the mobile element with at least four different weights, one after the other, and to ascertain the speed of vertical downward or upward movement of the mobile element under the action of each of these different weights. As mentioned above, the speed of the mobile element relative to the stationary element is proportional to (or can be utilized for ascertainment of) the viscosity of tested material.

In presently known viscometers wherein a rod or shaft moves vertically with respect to a stationary cylindrical or annular measuring element and wherein the sample of a material to be tested is introduced into a narrow annular clearance between the internal surface of the cylindrical or annular element and the periphery of the mobile element, the testing operation is carried out as follows: The mobile element is connected with a first weight and is allowed to move downwardly at a speed which is dependent on the mass of the weight and on viscosity of the sample, the mobile element is then returned to its starting position and the first weight is thereupon removed and replaced with a heavier second weight, and so forth. The just described conventional mode of testing is cumbersome and time-consuming as well as inaccurate, especially if each test is not preceded by introduction of a fresh sample into the aforementioned clearance. The introduction of a fresh sample is necessary for accuracy because the viscosity of a material which has been subjected to shearing stresses of first magnitude is not identical with the viscosity of the same material during subsequent application of shearing stresses of a different second magnitude. Nevertheless, many presently known viscometers are designed in such a way that a full series of tests is carried out with a single sample whereby the mobile measuring element moves from its starting position at a first speed during a first testing stage (when it is connected with a relatively small weight), from the same starting position but at a higher second speed during the next testing stage (as a result of connection of a heavier second weight), and so forth. Thus, the just described testing methods are carried out by utilizing one and the same sample in spite of the fact that such measurements are not entirely accurate due to the above-outlined properties of viscous materials (namely, that the viscosity changes in response to the application of shear stresses of different magnitude, one after the other, always to the same sample). The just mentioned characteristic of a viscous material is especially pronounced if the sample is subjected to different shear stresses at rapidly following intervals. The introduction of a fresh sample after each testing step is avoided because this would unduly prolong the duration of a complete test. Each individual testing step can take more than one minute. Moreover, and especially if the material to be tested is a highly viscous liquid or a paint (e.g., ink) which adheres to the stationary and mobile measuring elements, each introduction of a fresh sample must be preceded by lengthy, thorough and tedious cleaning of both measuring elements. Such situation will arise when the viscometer is used to ascertain the rheological properties of a series of inks, oil paints or the like.

OBJECTS AND SUMMARY OF THE INVENTION

An object of the invention is to provide a novel and improved viscometer which can complete a series of tests with substantial savings in time.

Another object of the invention is to provide a viscometer which can furnish accurate indications of the viscosity of a tested material even though it tests a single sample.

A further object of the invention is to provide novel and improved means for moving the mobile measuring element of a rod- or band-type viscometer with respect to the stationary measuring element.

An additional object of the invention is to provide the viscometer with novel and improved means for automatically varying the magnitude of shearing stresses upon different portions of a sample during a series of successive testing steps.

Another object of the invention is to provide the viscometer with novel and improved means for automatically preparing all mobile parts for the start of a series of successive testing steps.

An additional object of the invention is to provide a viscometer which can be readily adjusted to change the number and/or nature of steps in the course of a complete multi-stage testing operation.

Another object of the invention is to provide the viscometer with novel and improved means for coupling a series of weights to the mobile measuring element and to each other.

A further object of the invention is to provide a viscometer which need not be cleaned between successive steps or stages of a complete test and which can be used for accurate determination of the viscosity of a wide variety of different materials which are flowable at all times or at least in response to the application of a force.

The invention is embodied in a viscometer for testing the rheological properties of materials which are flowable, either at all times or at least in response to the application of deforming stresses. The viscometer comprises a stationary first measuring element (e.g., an upright cylinder), a vertically movable second measuring element (e.g., a vertical shaft which extends with clearance through the axial hole of the upright cylinder or a band or strip which extends with some clearance through a slit-shaped upright hole in the cylinder) which is adjacent to and defines with the first measuring element a preferably narrow clearance for introduction of a sample of a material to be tested (the material of the sample is subjected to shearing stresses during vertical movement of the second element with respect to the first element), and means for moving the second element vertically (normally downwardly, e.g., when the second measuring element is pulled at its lower end; however, a band-like element can move upwardly if it is trained over a pulley above the first measuring element and a pull is applied to that portion thereof which is remote from the portion extending through or otherwise cooperating with the first measuring element). In accordance with the invention, the means for moving the second measuring element comprises at least two discrete weights, means for connecting the weights to the second element so as to move the latter vertically with a predetermined force, and means for disconnecting one of the weights from the second element after elapse of an interval during which the second element moves through a predetermined distance so that the aforementioned predetermined force is reduced accordingly in response to disconnection of the one weight from the second element.

In accordance with a presently preferred embodiment of the invention, the connecting means includes means for securing the other weight to the lower end portion of a rigid or flexible second measuring element below the first measuring element. The one weight is then suspended and is normally spaced apart from the other weight, and the other weight is movable toward the one weight when the latter is held against downward movement. The disconnecting means then comprises a stop (e.g., a platform in the housing of the viscometer) which is located below the one weight so that the latter comes to rest on the stop after the second element descends through the aforementioned distance while the other weight is free to descend toward the thus arrested one weight.

The downward movement of the second element is terminated when the other weight reaches and comes to rest on the arrested one weight.

The viscometer preferably further comprises means for centering the other weight with respect to the second element during or at least prior to vertical movement of the second measuring element. Such centering means may comprise a carrier which is guided along a vertical tie rod and has a bifurcated portion or cradle for the weight nearest to the second measuring element.

The novel features which are considered as characteristic of the invention are set forth in particular in the appended claims. The improved viscometer itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
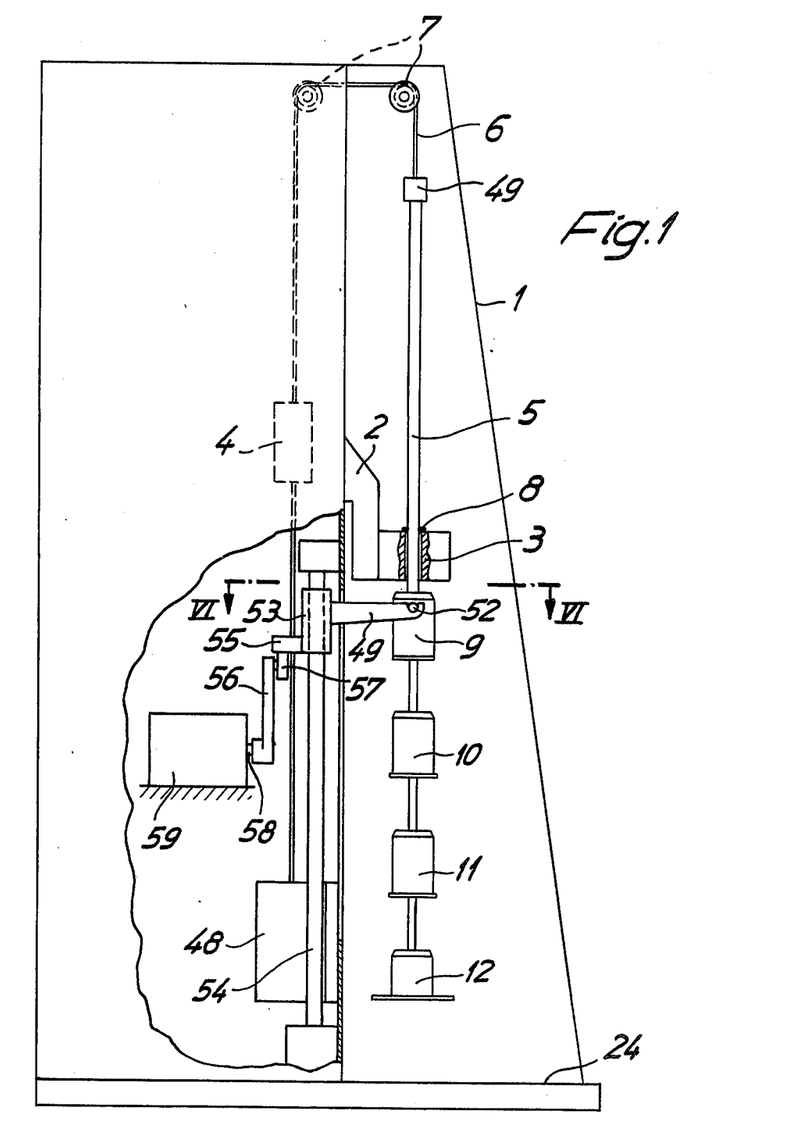
FIG. 1 is a somewhat schematic partly elevational and partly sectional view of a viscometer which embodies one form of the invention.

FIG. 1 shows a viscometer having a housing 1 for a supporting arm 2 which carries an upright cylinder 3 constituting one measuring element of the viscometer proper. The other measuring element is an elongated rod or shaft 5 (which can be replaced by a cord, band or strip if the cylindrical hole of the cylinder 3 is replaced with a slit) which is suspended from one end of a cable 6. The weight of the shaft 5 is at least partially balanced by a counterweight 4. The cable 6 (this term is used to denote a cord, a wire, a rope, a tape or any other suitable flexible element) is trained over pulleys 7 which are mounted in the housing 1 at a level above the supporting arm 2. It is clear that the counterweight 4 constitutes but one form of means for balancing the weight of the shaft 5; for example, the left-hand portion of the cable 6 can be biased downwardly, as viewed in FIG. 1, by one or more springs (not shown). The right-hand end portion of the cable 6 is attached to a permanent magnet 49 which attracts the magnetizable upper end portion of the shaft 5 so that the latter can be readily separated from the cable (e.g., for the purpose of cleaning that portion which slides through the axial hole of the cylinder 3) by overcoming the magnetic attracting force of the magnet 49.

Figure 2:
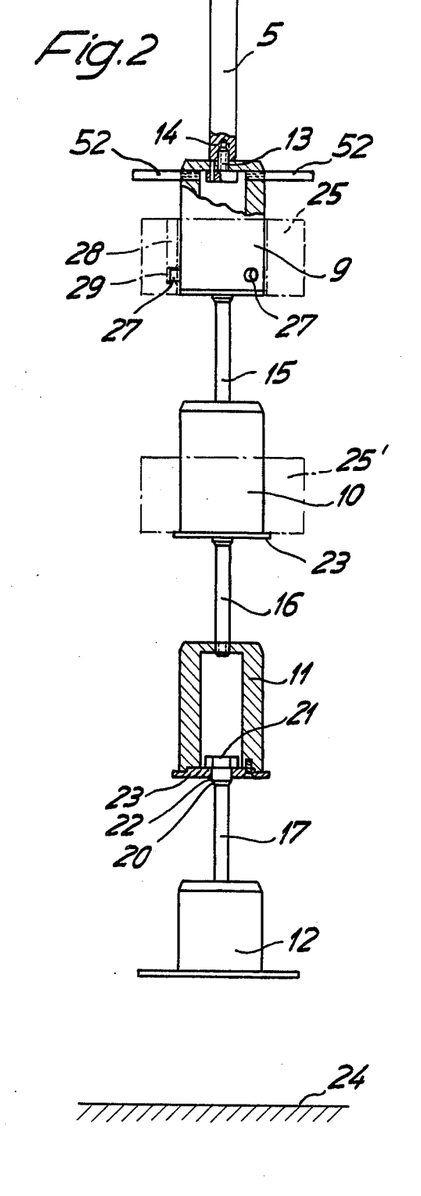
FIG. 2 is an enlarged view of a detail in FIG. 1, showing the manner in which several weights are connected to each other and to the mobile measuring element, two of the weights and a portion of the mobile measuring element being shown in section.
Figure 3:
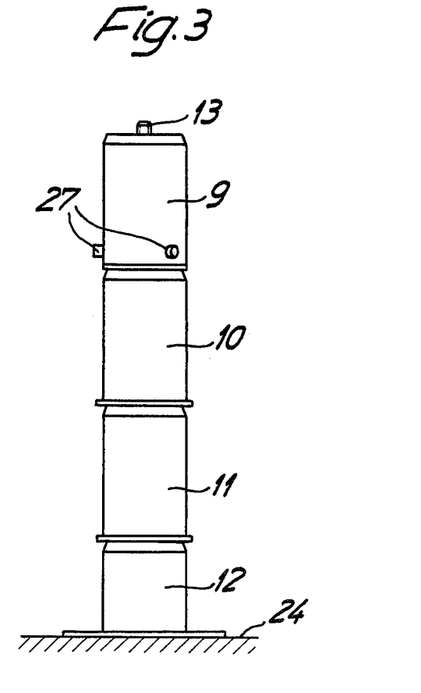
FIG. 3 is a side elevational view of the weights of FIG. 2 in the positions they assume upon completion of a multi-stage test.

That portion of the shaft 5 which extends through the hole of the cylinder 3 defines with the internal surface of the cylinder a cylindrical clearance or gap 8 for introduction of a sample of the material whose rheologic properties require determination. For example, such material may constitute a highly viscous paint, adhesive or the like. The material is subjected to shearing stresses as a result of movement of the shaft 5 relative to the cylinder 3. To this end, the lower end portion of the shaft 5 (at a level below the cylinder 3) is coupled to several weights 9, 10, 11 and 12 in a manner which is illustrated in FIGS. 2 and 3. The provision of several weights renders it possible to perform a multi-stage test and to plot an appropriate viscosity curve which is indicative of the rheologic properties of the sample in the clearance 8.

FIG. 2 shows that the uppermost weight 9 comprises an upwardly extending male coupling portion or stud 13 received in a tapped bore 14 machined into the lower end and face of the shaft 5. The positions of the stud 13 and tapped bore 14 can be reversed.

The weights 9–10, 10–11 and 11–12 are respectively coupled to each other by rods 15, 16 and 17. The lower end portion of the rod 15 has external threads which mate with the internal threads (not shown) machined into the upper end portion of the weight 10. The manner in which the rods 16 and 17 are attached to the weights (11, 12) therebelow is the same. The mode of movably connecting the upper end portions of the rods 15, 16, 17 to the lower portions of the weights thereabove is illustrated in FIG. 2 in connection with the rod 17 and weight 11. The weight 11 is hollow and its bottom wall 23 has a centrally located bore 22 which snugly receives an enlarged cylindrical portion 20 of the rod 17 when the latter is fully exposed, i.e., when the weights 11 and 12 are located at a maximum distance from each other. The enlarged portion 20 is located below a head 21 which abuts against the upper side of the bottom wall 23 and prevents accidental separation of the rod 17 from the weight 11.

FIGS. 1 and 2 show the four weights 9 to 12 at a maximum distance from each other. The weights 9–12 assume such positions prior to start of a measurement. In FIG. 3, the weights 9–12 are shown in fully condensed condition, i.e., the lowermost weight 12 rests on a platform or stop 24 in the housing 1 and the weights 9, 10, 11 respectively rest on the weights 10, 11 12 therebelow. The rods 15, 16, 17 are completely concealed in the interior of the respective weights 9, 10 and 11.

Figure 4:
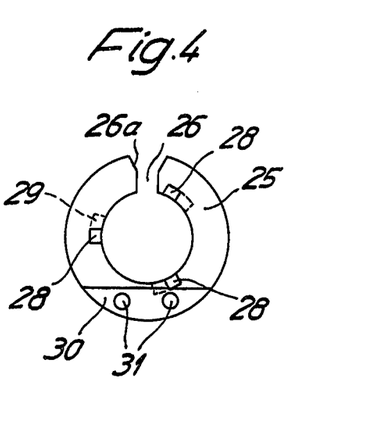
FIG. 4 is a plan view of an auxiliary weight which can be used in the viscometer of FIG. 1.

FIG. 4 shows an auxiliary weight 25 which can be mounted on the uppermost weight 9 of the row of weights 9–12. The auxiliary weight 25 is a ring-shaped body having a radial slot 26 and a central opening large enough to receive the weight 9. The slot 26 is flanked by surfaces whose outer portions 26a flare outwardly to facilitate the placing of the auxiliary weight 25 in register with the weight 9 between the weights 9 and 10, i.e., the slot 26 permits entry of the rod 15 into the central opening of the auxiliary weight 25. The quick-release connection between the weights 9 and 25 includes a bayonet type lock. The bayonet lock comprises three radially outwardly extending pins 27 at the periphery and close to the bottom wall of the weight 9 (two pins 27 are shown in FIG. 2). These pins can be received in L-shaped slots having vertical portions 28 extending upwardly from the bottom end face and machined into internal surface of the auxiliary weight 25, and horizontal portions 29 which communicate with the upper ends of the respective vertical portions 28. The weights 10–12 do not have pins 27 because their bottom walls 23 extend radially beyond the peripheral surfaces of their major portions and, therefore, the auxiliary weight 25 could not be slipped (from below) onto the weights 10–12 in the same way as onto the uppermost weight 9.

The auxiliary weight 25 is further provided with a cutout 30 which is located diametrically opposite the slot 26. The purpose of the cutout 30 is to keep the auxiliary weight 25 in balance, i.e., to insure that identical or nearly identical quantities of material are removed from the auxiliary weight at both sides of the symmetry plane which extends horizontally (as viewed in FIG. 4) and includes the axis of the weight 25. The auxiliary weight 25 is or can be provided with additional weights 31 in the form of detachable pins or the like which serve to insure that the resultant force of all weights acts in the axial direction of the shaft 5. FIG. 2 shows, by broken lines, the manner in which the auxiliary weight 25 is mounted on the weight 9, and a second auxiliary weight 25' which simply rests on the marginal portion of the bottom wall 23 of the weight 10.

The weight 25 can be heavier or lighter than the weight 25'. Furthermore, the viscometer can be furnished with an entire set of auxiliary weights including weights which can be attached to the uppermost weight 9 and/or weights which can be attached to the weight 10, 11 and/or 12. Furthermore, and as already described in connection with FIG. 4 (pins 31), the mass of an auxiliary weight can be changed to insure the application of an optimum force to the mobile measuring element 5. The combined mass of all weights, the mass of each individual weight and the mass of each auxiliary weight (if any) will be selected in dependency on that range of viscosities which is to be ascertained in the improved apparatus.

The length of the coupling rods 15 should be selected in such a way that the interval during which the shaft 5 descends before the lowermost weight 12 reaches the stop 24, before the weight 11 comes to rest upon the arrested weight 12, and so on is long enough to allow for accurate recording of the speed and/or another parameter which is indicative of viscosity. For example, and if the speed is measured only during a fraction of each of the aforementioned intervals, the timer which determines the start and termination of velocity measurement can be set in such a way that the measurement is terminated before the weight 12 strikes against the stop 24 or before a weight (9, 10 or 11) comes to rest on the weight (10, 11, 12) therebelow. This eliminates from the measurement that instant or period during which a weight becomes detached from the mobile measuring element. Such detachment can create shocks which, if ascertained by the instrument 48 of FIG. 1, could result in distortion of the viscosity curve.

Figure 5:
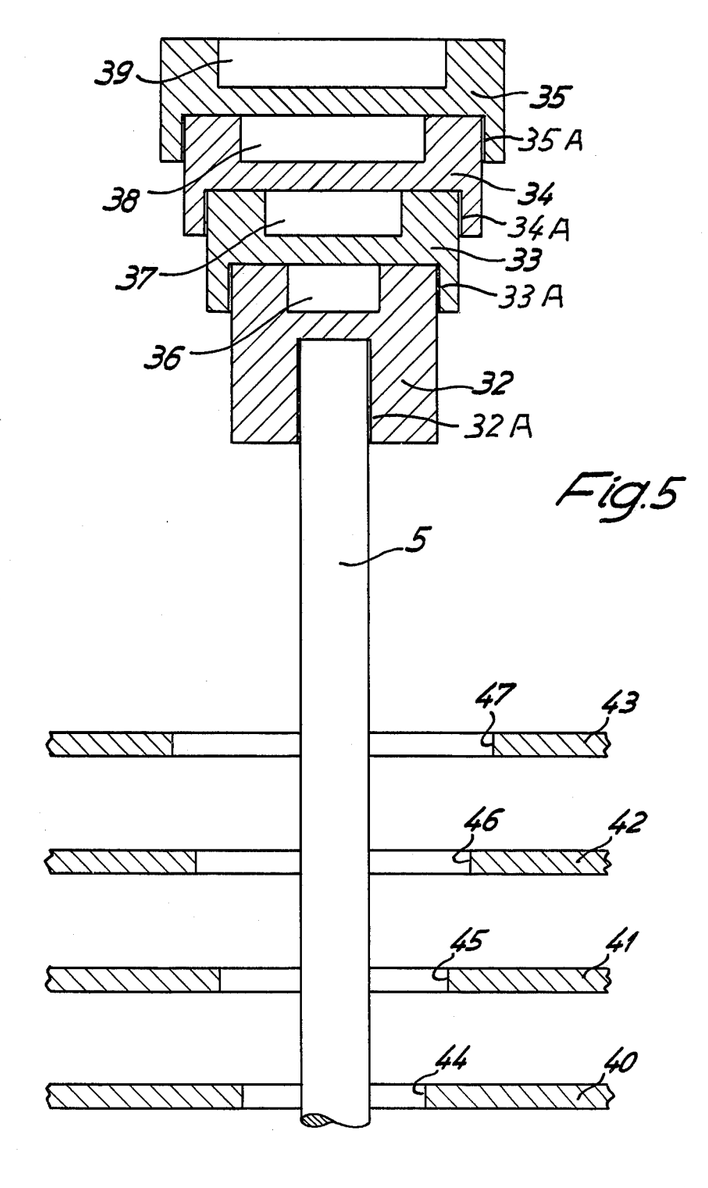
FIG. 5 is a fragmentary elevational view of a mobile measuring element and an axial sectional view of a group of modified weights and of intercepting means for such weights.

FIG. 5 shows a modified viscometer wherein four weights 32, 33, 34 and 35 are mounted at the upper end of the shaft 5. Each of the weights 33, 34, 35 receives a portion of the weight (32, 33, 34) therebelow, i.e., the weights 32–35 are stacked in such a way that each lower weight extends in part into the interior of the weight immediately thereabove. The undersides of the weights 32–35 are respectively formed with sockets or blind bores 32A, 33A, 34A, 35A for the upper end portion of the shaft 5 and for the upper end portions of the weights 32, 33, 34. In addition, the upper end faces of the weights 32–35 are respectively formed with cavities 36, 37, 38, 39 which (if necessary) can receive auxiliary weights (not shown) in the form of disks, rings or the like.

In order to enable the viscometer which embodies the structure of FIG. 5 to carry out a multi-stage test, the apparatus further comprises four disconnecting or intercepting devices 40, 41, 42 and 43 having openings 44, 45, 46, 47 through which the shaft 5 extends downwardly toward and through the cylinder 3 (not shown in FIG. 5). The diameter of the opening 47 in the uppermost intercepting device 43 (e.g., a stationary horizontal plate) permits the passage of weights 32–34 but is smaller than the outer diameter of the uppermost weight 35 so that the latter is intercepted by the device 43. Analogously, the opening 46 permits the passage of the weights 32, 33 but the device 42 intercepts the weight 34, the device 41 intercepts the weight 33 but permits the weight 32 to pass through the opening 45, and the device 40 intercepts the weight 32 while permitting the shaft 5 to pass through its opening 44. Thus, as the shaft 5 descends, the force with which it is urged downwardly decreases stepwise as the devices 43, 42, 41, 40 respectively intercept the weights 35, 34, 33, 32 in such order.

The structure of FIG. 5 can be modified in a number of ways without departing from the spirit of the invention. For example, the shaft 5 can support a stack of two, three, four or even more weights having identical outer diameters or other than circular outlines. Each weight carries one or more radially outwardly extending arms, and the arms of neighboring weights are angularly offset with respect to each other. The arms of the weights below the uppermost weight can pass through suitable slots or recesses of an intercepting device for the arms of the uppermost weight, the arms of the weights below the next-to-the-uppermost weight can pass through the slots of a second device, and so forth, i.e., the arrangement is clearly analogous so that shown in FIG. 5.

Referring again to FIG. 1, the cable 6 passes through a measuring instrument or detector 48 which is disposed at a level below the counterweight 4 and is installed in the housing 1. The detector 48 monitors the speed of movement of the cable 6 and hence the speed of movement of the shaft 5 during successive stages of a multi-stage testing operation, namely while the shaft 5 is biased by different numbers of weights. Such measurements of velocity of the shaft 5 can be utilized to ascertain the viscosity of the sample in the clearance 8 between the shaft 5 and cylinder 3. The viscosity is ascertained by knowing the momentary weight upon the shaft 5 and the speed of the shaft.

The manner in which the instrument 48 can be used to plot a flow curve is disclosed, for example, in "American Ink Maker," May 1961, pages 62 et seq.

The feature that the cable 6 is trained over the pulleys 7 is desirable and advantageous because it contributes to compactness of the viscometer and also because the counterweight 4 can readily compensate for the weight of the shaft 5. Thus, the detector 48 can be installed adjacent to rather than at a level above or below the shaft 5.

Figure 6:
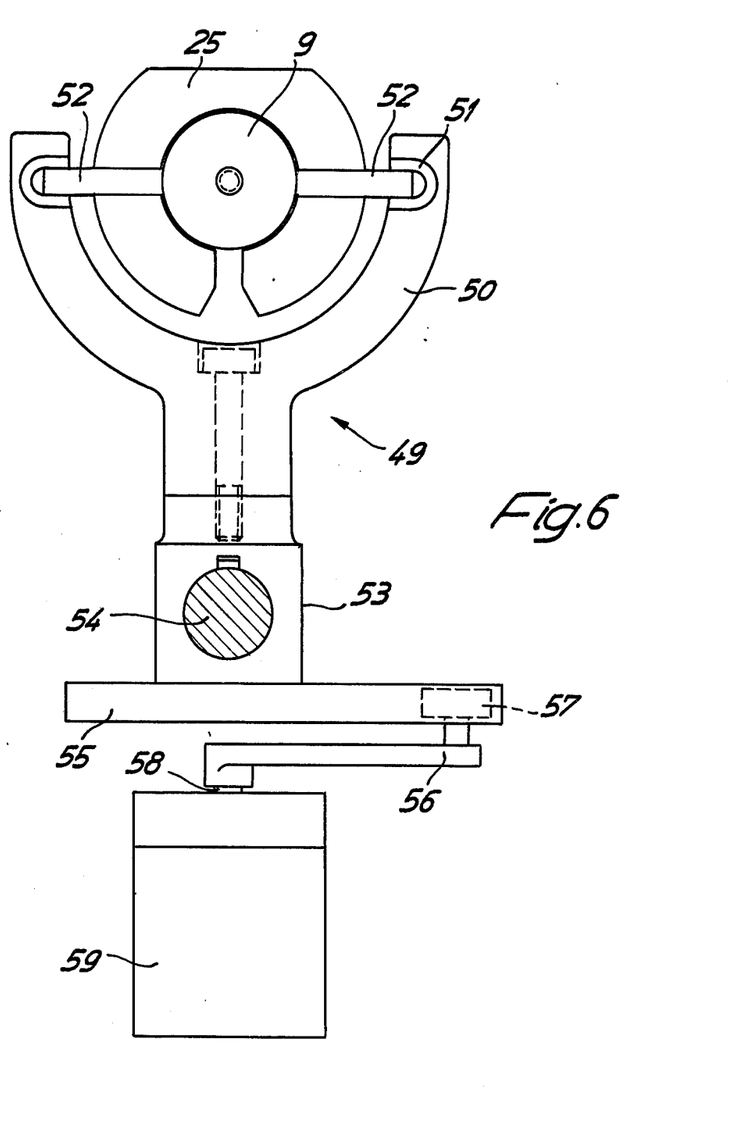
FIG. 6 is an enlarged horizontal sectional view as seen in the direction of arrows from the line VI—VI of FIG. 1.

The viscometer further comprises means for moving the weights 9–12 up or down and for centering these weights in the starting positions (FIG. 2) prior to the beginning of a fresh test. The details of such means are shown in FIGS. 1 and 6. A carrier 49 has a bifurcated centering portion or cradle 50 with two prongs each of which is formed with a socket 51 bounded by a conical surface. The sockets 51 receive the outer end portions of two coaxial studs 52 which are mounted on or made integral with the weight 9 and are disposed diametrically opposite each other with respect to the axis of the shaft 5. The conical configuration of surfaces bounding the sockets 51 insures automatic centering of the weight 9 when the latter is suspended on the bifurcated portion 50 of the carrier 49. At the same time, the conical surfaces bounding the sockets 51 insure automatic centering of the shaft 5 (which is coaxial with the weight 9) and of the other weights 10–12 as well as of one or more auxiliary weights (25, 25'), if any.

The carrier 49 further comprises a follower sleeve 53 which is located opposite the bifurcated portion 50 and is slidable along an upright tie rod or guide 54 mounted in the housing 1 in parallelism with the shaft 5. The follower 53 has a transversely extending horizontal channeled motion receiving member 55 for the roller-shaped wiper 57 at the free end of a crank arm 56 mounted on the output shaft 58 of a prime mover 59, e.g., an electric motor. The wiper 57 may constitute the outer race of a ball or roller bearing. The just described means for moving the follower 53 up and down along the guide 54 is dimensioned and mounted in such a way that the weights 9–12 are held in the starting positions in the upper dead-center position of the crank arm 56. As the crank arm 56 rotates beyond such dead center position so that the wiper 57 leaves the center of the groove of the channel-shaped motion transmitting member 55, the carrier 49 is free to descend whereby the guide 54 insures that the carrier moves along a vertical path.

The carrier 49 insures that each of the weights 9–12 assumes an optimum position with respect to the shaft 5 prior to start of a multi-stage test. This facilitates the introduction of a fresh sample because both hands of the attendant are free, i.e., the attendant need not grasp the weight 9 in order to maintain the latter in the position of FIG. 1 or 2. Moreover, the attendant can determine or initiate the start of a multi-stage test at his or her leisure, namely, upon completion of introduction of a fresh sample and as soon as the motor 59 is started to move the crank arm 56 from the upper dead center position. It will be appreciated that the motor 59 can be activated to abruptly release the shaft 5 for movement under the combined action of the weights 9–12 or to effect a gradual movement of the channeled member 55 from the upper end position.

The provision of the means 49–59 for lifting the weights 9–12 to the positions of FIG. 1 or 2 also facilitates the manipulation of the viscometer and shortens the periods of idleness between successive tests. The motor 59 can further serve to move the shaft 5 up or down (once or more than once) prior to start of a multi-stage test in order to insure that the material of a freshly introduced sample completely coats the internal surface of the cylindrical element 3 as well as the entire external surface of that portion of the shaft 5 which extends through the element 3 prior to start of a multi-stage test. Finally, the motor 59 performs work (lifting of weights 9–12 from the positions of FIG. 3 to the positions of FIG. 1 or 2) which would be tiresome to an attendant, especially after completion of a large number of successive tests. All the attendant has to do is to activate the controls for the motor 59, to admit fresh samples into the clearance 8 and to clean the measuring elements 3,5 after completion of each multi-stage test.

The rate at which the carrier 49 descends in response to movement of the crank arm 56 from the upper dead center position is always higher than the rate of downward movement of the shaft 5 under the combined action of the weights 9–12. This insures that the carrier 49 cannot adversely influence the testing operation, i.e., that the speed at which the shaft 5 descends depends solely on the force which is applied by the weight or weights and on the resistance of the sample in the clearance 8.

An important advantage of the improved viscometer is that its accuracy greatly exceeds the accuracy of heretofore known viscometers which employ a vertically movable measuring element. This is due to the fact that the descending shaft 5 (or a band or strip which can move up or down) continuously draws fresh material from the clearance so that the altered viscosity of a sample portion which was removed during the preceding stage of a multi-stage testing operation cannot influence the viscosity of that portion of the sample which is withdrawn from the clearance when the number of weights acting upon the mobile measuring element is changed. As mentioned above, presently known rod- or band-type viscometers are operated in such a way that the rod or band is caused to move through a given distance in response to attachment of a first weight, that the rod or band is thereupon returned to starting position prior to attachment of a different second weight, and so forth. Therefore, one and the same portion of a sample is moved up and down, together with the rod or band, so that the altered viscosity of such portion of the sample affects the accuracy of measurements which are carried out with the second, third, etc., weights.

It is preferred, at this time, to employ weights which are suspended on the mobile measuring element, i.e., which are disposed at a level below the stationary measuring element, because such mounting of weights is less likely to cause the mobile measuring element to tilt or to otherwise leave the position of accurate alignment with the stationary measuring element. Moreover, the structure which is shown in FIG. 5 is suitable only for use in connection with rod- or shaft-like (rigid) mobile measuring elements.

It will be noted that, in contrast with the mode of operation of conventional viscometers, the improved apparatus ascertains the viscosity of a flowable material by subjecting a first portion of a sample to a maximum shearing stress, by thereupon subjecting another portion of the sample to a less pronounced shearing stress, and so on. The distance which the mobile measuring element covers during each interval which elapses while the sample is subjected to a shearing stress of given magnitude must be sufficient to enable the instrument 48 to ascertain and record the speed of the mobile measuring element. In fact, it is possible to provide for a certain amount of idling (additional lengthwise movement) of the mobile measuring element to insure that the instrument will properly evaluate the results of the corresponding stage of a multi-stage testing operation.

The feature that the weights 9-12 or 32-35 are disconnected from the mobile measuring element in automatic response to lengthwise movement of such element renders it possible to achieve substantial savings in time, i.e., the interval for completion of a four-stage test is a small fraction of the interval which elapses during testing of one and the same portion of a sample in accordance with the aforediscussed conventional methods which involve repeated movement of the mobile measuring element to starting position and the attachment of an additional weight (or the replacement of a lighter weight with a heavier weight) whenever the mobile measuring element returns to the starting position.

As mentioned before, a multi-stage test is desirable in order to ascertain several points of a viscosity curve which denotes the rheologic properties of the sample. Since the measuring elements need not be cleaned after each stage of a multi-stage test, the servicing of the viscometer is much simpler than that of a conventional apparatus wherein the measuring elements must be cleaned after each stage if the multi-stage test is to furnish an accurate indication of viscosity. Removal of highly viscous and/or colored liquids from the measuring elements is likely to result in contamination of hands, garments and/or parts of the apparatus other than the measuring elements.

The term "disconnecting" or "detaching," as used in the appended claims, is intended to embrace complete detachment of successive weights (or at least one weight) from the mobile measuring element as well as mere separation in a sense or to the extent that the weight cannot act upon the mobile measuring element for the purpose of moving the latter with respect to the stationary measuring element. Thus, the weights 9-12 of FIG. 3 are "detached" or "disconnected" from the shaft 5, even if the latter is connected to the threaded member 13, because the weights rest on the stop 24 and, consequently, cannot promote the movement of the shaft 5 relative to the cylindrical measuring element 3.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

What is claimed is:

1. In a viscometer for testing the rheological properties of materials which are flowable at least in response to the application of deforming stresses thereto, the combination of a stationary first measuring element; a vertically movable second measuring element adjacent to and defining with said first element a clearance for reception of a sample of the material to be tested, such material being subjected to a shear stress during vertical movement of said second element; and means for moving said second element vertically, including at least two discrete weights, means for connecting said weights to said second element so as to move the latter vertically with a predetermined force, and means for disconnecting at least one of said weights from said second element after elapse of an interval during which said second element moves through a predetermined distance so that said force is reduced accordingly in response to disconnection of said one weight.

2. The combination of claim 1, wherein said second element has a lower end portion and said connecting means includes means for securing the other of said weights to said lower end portion, said one weight being suspended on and being normally spaced apart from said other weight and said other weight being movable toward said one weight when the latter is held against downward movement, said disconnecting means including a stop located below said one weight so that the latter comes to a rest on said stop after said second element descends through said distance while said other weight is free to descend toward the thus arrested one weight.

3. The combination of claim 2, wherein the downward movement of said second element is terminated when said other weight reaches and comes to rest on the arrested one weight.

4. The combination of claim 2, further comprising means for centering said other weight with respect to said second element prior to vertical movement of said second element.

5. The combination of claim 4, wherein said centering means is movable to and from an upper end position and includes means for lifting said other weight and said second element to a starting position prior to testing of a fresh sample in said clearance, and further comprising means for moving said centering means to said starting position and for thereupon permitting said centering means to descend faster than said other weight and said second measuring element.

6. The combination of claim 5, wherein said last mentioned moving means comprises a crank arm rotatable about a horizontal axis and movable to and from an upper dead center position in which said second element is held in said starting position.

7. The combination of claim 2, wherein the normal spacing of said weights at least equals a distance which is required to ascertain the velocity of the second element before said one weight reaches said stop.

8. The combination of claim 2, further comprising means for coupling said one weight with said other weight, said coupling means including a rod having an end portion secured to one of said weights and being reciprocable in the other of said weights to the extent which is necessary to enable said first mentioned other weight to come to rest on said first mentioned one weight on further downward movement of said second element subsequent to stoppage of said first mentioned one weight.

9. The combination of claim 8, wherein said rod includes a head at the other end thereof and said last mentioned other weight has an end wall with a bore large enough for the major portion of said rod but preventing the extraction of said head from the interior of said last mentioned other weight.

10. The combination of claim 9, wherein said rod has an enlarged portion which is adjacent to said head and is snugly received in said bore when said weights are disposed at a maximum distance from each other.

11. The combination of claim 1, further comprising means for balancing the weight of said second measuring element so that the weight of such element does not influence the rate of vertical movement thereof.

12. The combination of claim 11, further comprising at least one pulley disposed above said first element and a cable trained over said pulley and having a first portion disposed at one side of said pulley and connected to said second measuring element and a second portion at the other side of said pulley, said balancing means including a counterweight attached to said second portion of said cable.

13. The combination of claim 12, wherein said second measuring element comprises an upper end portion consisting of magnetizable material and further comprising a permanent magnet attached to said first portion of said cable, said end portion of said second element adhering to said magnet.

14. The combination of claim 1, wherein said first element includes a cylinder having an upright cylindrical hole and said second measuring element is a shaft which is reciprocable in said hole.

15. The combination of claim 1, wherein said second measuring element is flexible.

16. The combination of claim 1, wherein said second element is a rigid shaft having an upper end portion above said clearance and said weights are mounted on the upper end portion of said second element.

17. The combination of claim 16, wherein said one weight is disposed above said other weight and said disconnecting means comprises a device arranged to intercept said one weight after said second element decends through said distance.

18. The combination of claim 1, further comprising at least one auxiliary weight and means for connecting said auxiliary weight to one of said first mentioned weights.

19. The combination of claim 1, wherein the resultant force which said weights apply to said second element acts in the axial direction of said second element.

20. The combination of claim 1, further comprising means for movably coupling said weights to each other and at least one auxiliary weight having a slot for said coupling means and means for attaching said auxiliary weight to one of said first mentioned weights.

21. The combination of claim 20, further comprising at least one additional weight provided on said auxiliary weight.

22. The combination of claim 20, wherein said auxiliary weight is an annulus and said slot extends substantially radially of said annulus, said annulus further having a cutout disposed substantially diametrically opposite said slot.

23. The combination of claim 20, wherein said attaching means comprises a bayonet lock.

* * * * *